US008696566B2

(12) United States Patent
Cho et al.

(10) Patent No.: US 8,696,566 B2
(45) Date of Patent: Apr. 15, 2014

(54) METHOD FOR ANALYZING STRESS BASED ON MULTI-MEASURED BIO-SIGNALS

(75) Inventors: Chul-Ho Cho, Seongnam-si (KR); Desok Kim, Daejeon (KR); Jae-Geol Cho, Yongin-si (KR); Sun-Tae Jung, Yongin-si (KR); Salahuddin Lizawati, Daejeon (KR)

(73) Assignees: Samsung Electronics Co., Ltd., Samsung-ro, Yeongtong-gu, Suwon-si, Gyeonggi-do (KR); Information and Communications University, Research and Industrial Cooperation Group, Munji-dong, Yuseong-gu, Daejeon (KR)

( * ) Notice: Subject to any disclaimer, the term of this patent is extended or adjusted under 35 U.S.C. 154(b) by 739 days.

(21) Appl. No.: 12/208,413

(22) Filed: Sep. 11, 2008

(65) Prior Publication Data

US 2009/0069641 A1    Mar. 12, 2009

(30) Foreign Application Priority Data

Sep. 11, 2007    (KR) .............................. 2007-0092185

(51) Int. Cl.
*G06F 19/00* (2011.01)
*A61B 5/00* (2006.01)

(52) U.S. Cl.
USPC ................................. 600/300; 600/301; 705/2

(58) Field of Classification Search
None
See application file for complete search history.

(56) References Cited

U.S. PATENT DOCUMENTS

| 5,304,112 | A  | * | 4/1994 | Mrklas et al. | 600/27 |
| 6,358,201 | B1 | * | 3/2002 | Childre et al. | 600/300 |
| 2001/0049471 | A1 | * | 12/2001 | Suzuki et al. | 600/300 |
| 2003/0097047 | A1 | * | 5/2003 | Woltermann et al. | 600/300 |
| 2003/0236451 | A1 | * | 12/2003 | El-Nokaly et al. | 600/300 |
| 2004/0117212 | A1 | * | 6/2004 | Kong et al. | 705/2 |
| 2005/0154264 | A1 | * | 7/2005 | Lecompte et al. | 600/300 |
| 2006/0206010 | A1 | * | 9/2006 | Iida et al. | 600/300 |
| 2007/0150309 | A1 | * | 6/2007 | Taylor et al. | 705/2 |
| 2008/0195980 | A1 | * | 8/2008 | Morris | 715/864 |

FOREIGN PATENT DOCUMENTS

KR    20-0304913 Y1    2/2003
KR    10-2003-0034424 A    5/2003

OTHER PUBLICATIONS

Mi-hee Lee; Yang, G.; Lee, H.-K.; Bang, S.; , "Development stress monitoring system based on personal digital assistant (PDA)," Engineering in Medicine and Biology Society, 2004. IEMBS '04. 26th Annual International Conference of the IEEE , vol. 1, No., pp. 2364-2367, Sep. 1-5, 2004 doi: 10.1109/IEMBS.2004.1403685 URL: http://ieeexplore.ieee.org/.*

(Continued)

*Primary Examiner* — Bill Thomson
*Assistant Examiner* — Davin K Sands
(74) *Attorney, Agent, or Firm* — Cha & Reiter, LLC.

(57) ABSTRACT

Disclosed is a method and system for analyzing stress and managing stress by using a mobile electronic apparatus and a data management server. The method includes: generating bio-signal pattern information upon periodically receiving a bio-signal from a bio-signal measuring device connected to each of a plurality of unspecified individuals, and forming reference information for stress analysis based on received answers to each of a plurality of questions for checking a stress level; receiving bio-signal pattern information from a bio-signal measuring device connected to a specified user; and determining a stress level corresponding to the bio-signal pattern information of the specified user based on the reference information.

17 Claims, 9 Drawing Sheets

(56) References Cited

OTHER PUBLICATIONS

Mi-hee Lee; Yang, G.; Lee, H.-K.; Bang, S.; , "Development stress monitoring system based on personal digital assistant (PDA)" Engineering in Medicine and Biology Society, Sep. 2004. 26th IEEE Intl Conf, vol. 1, pp. 2364-2367, 1-5 doi: 10.1109/IEMBS.2004.1403685 URL: http://ieeexplore.ieee.org/stamp/stamp.jsp?tp=&arnumber=1403685&isnumber=30462.*

* cited by examiner

| IDENTIFICATION NUMBER | SEX DISTINCTION | AGE RANGE | BIOSIGNAL PATTERN INFO | SCORE OF ANSWER RESULT OF SRI | STRESS LEVEL |
|---|---|---|---|---|---|
| 130001 | M | 30~33 | $3X^2+2X+1$ | 30 | LOW |
| 130002 | M | 30~33 | $X^2+X+4$ | 28 | LOW |
| 130003 | M | 30~33 | $2X^2+3X+3$ | 43 | MIDDLE |
| 130004 | M | 30~33 | $X^2+3X+1$ | 86 | HIGH |
| ... | ... | ... | ... | ... | ... |
| 225001 | F | 23~26 | $2X^2+3X+3$ | 92 | HIGH |
| 225002 | F | 23~26 | $X^2+3X+1$ | 40 | MIDDLE |
| ... | ... | ... | ... | ... | ... |

(Row 130002 highlighted — INDIVIDUAL REFERENCE INFO)

FIG.9

METHOD FOR ANALYZING STRESS BASED ON MULTI-MEASURED BIO-SIGNALS

CLAIM OF PRIORITY

This application claims the benefit of the earlier filing date, under 35 U.S.C. §119(a), to that patent application entitled "Method for Analyzing Stress Based on Multi-Measured Bio-signals," filed in the Korean Intellectual Property Office on Sep. 11, 2007 and assigned Serial No. 2007-0092185, the contents of which are incorporated herein by reference.

BACKGROUND OF THE INVENTION

1. Field of the Invention

The present invention relates to a method for analyzing stress in a mobile environment, and more particularly to a method for measuring a Circadian rhythm Variability (CV) of bio-signals (i.e. a pattern of biological signals on a daily cycle) by using a mobile sensor and a mobile terminal and analyzing stress by using the measured CV.

2. Description of the Related Art

Generally, stress causing a person to internally feel strain (or tension) in their physical and/or mental condition. Stress causes inconvenience in stability of the mind or living along with other people, or causes physical and mental strain. Stress, accordingly, refers to an uncharacteristic response of a body caused by pressure imposing a certain burden on bodily organs, whether the pressure is pleasant one or not. A response to temporal stress caused by an external environment may be a natural phenomenon, but when a bodily response to the stress persists for a long time, mental and physical damage may occur. Accordingly, in order to prevent damage due to the stress from occurring, known methods for measuring and easing stress have been used.

A level of stress can be determined either by measuring a biological change due to the stress using an apparatus for measuring a bio-signal or by an evaluation (e.g., an interview) with a medical specialist.

Further, since stress may temporarily occur due to external factors, it is desirable to measure stress considering the external factors. In order to analyze chronic stress, it is desirable to continuously measure chronic stress and analyze a change transition of the measured chronic stress. However, since there is a limit to the method for measuring stress, there have been many cases where stress cannot be measured with a proper consideration of the changes in the user's environment.

Meanwhile, with recent advances in electronic technology, it is possible to measure a bio-signal by using a mobile sensor, and with the wide spread of mobile communication apparatuses, many people are using mobile communication terminals. By using a mobile communication terminal as described above, it is possible to immediately and continuously measure stress. Accordingly, there has been a requirement for a method in which a user can easily and accurately measure a stress state by using an apparatus carried by an individual.

SUMMARY OF THE INVENTION

Accordingly, the present invention provides a method in which a user can easily, and accurately, measure and analyze stress in a mobile environment including a mobile sensor and a mobile terminal.

Also, the present invention provides a stress analysis method which can continuously measure stress and reduce errors in measuring stress, in order to quantitatively manage chronic stress which can be a cause of a serious disease.

In accordance with an aspect of the present invention, there is provided a method for analyzing stress, the method including the steps of 1) generating bio-signal pattern information upon periodically receiving a bio-signal from a bio-signal measuring device connected to each of unspecified individuals and receiving an answer to each of questions for checking a stress level, and forming reference information for stress analysis based on the bio-signal pattern information and the answer; 2) receiving bio-signal pattern information from a bio-signal measuring device connected to a specified user; and 3) determining a stress level corresponding to the bio-signal pattern information of the specified user based on the reference information.

The method may further include a step of displaying the determined stress level on a display.

Also, the method may further include a step of displaying additionally included information enabling reduction of a stress level in response to the determined stress level.

Step 1) may include the sub-steps of: providing questions for checking a stress level, and determining a stress level of a user upon receiving an answer to each of the questions; generating bio-signal pattern information upon periodically receiving a bio-signal from each of the bio-signal measuring devices; storing the bio-signal pattern information in connection with the stress level; and forming reference information for stress analysis in consideration of the bio-signal pattern information and the stress level.

Preferably, the bio-signal corresponds to a Heart Rate Variability (HRV), and is measured by a mobile sensor for sensing a heart rate and a heart rate measurement module for converting a signal received as an input from the mobile sensor into data representing an HRV.

Preferably, the heart rate measurement module requests measurement of a bio-signal at every predetermined cycle.

Preferably, the heart rate measurement module is mounted in a mobile terminal.

The bio-signal pattern information includes a maximum value or a minimum value of a periodically-measured HRV.

In accordance with another aspect of the present invention, there is provided a system for managing stress by using a mobile electronic apparatus and a data management server, the system including: at least one mobile electronic apparatus; and a stress management server, wherein each of the at least one mobile electronic apparatus includes: a bio-signal measuring device for measuring a bio-signal of a user; a bio-signal pattern information generation unit for combining bio-signals, each of which is periodically received as an input from the bio-signal measuring device, and generating bio-signal pattern information; an individual reference information generation unit for outputting a Stress Response Inventory (SRI) questionnaire for checking a stress level of the user, receiving an answer to each question of the SRI questionnaire, driving the bio-signal measuring device and the bio-signal pattern information generation unit, and generating individual reference information obtained by connecting the result of answering the SRI questionnaire with the pattern information of the measured bio-signals; and a stress analysis request unit for transmitting the pattern information of the measured bio-signals to a stress management server, and requesting analysis of a stress level of the user. In another aspect of the invention the stress management server includes: a reference information management unit for receiving the individual reference information from each of the at least one mobile electronic apparatus, and forming a DataBase (DB) of several pieces of the individual reference information; a bio-signal pattern information management unit for forming a DB of the bio-signal pattern information received from each of the at least one mobile electronic apparatus; and a stress level analysis unit for receiving a request for analysis of a stress level of the user from a specified mobile electronic apparatus, and analyzing the stress level.

The stress management server further includes: a site operating unit for managing data required for site operation; and a member information management unit for managing member information including identification information of each of the at least one mobile electronic apparatus, identification information of a user, a site IDentification (ID), and a pass word.

The bio-signal may correspond to a Heart Rate Variability (HRV), and the bio-signal measuring device may include: a mobile sensor for sensing a heart rate, and a heart rate measurement module for converting a signal received as an input from the mobile sensor into data representing an HRV.

Preferably, the heart rate measurement module includes an alarm for requesting measurement of a bio-signal at predetermined cycle or interval.

Preferably, the bio-signal pattern information includes a maximum value or a minimum value of a periodically-measured HRV.

Each of the at least one mobile electronic apparatus may be mounted in a mobile communication terminal.

Preferably, each of the at least one mobile electronic apparatus includes a storage medium for storing multiple SRI questionnaires therein, and selectively outputs some of the multiple SRI questionnaires as the need arises.

Preferably, the stress management server includes a storage medium for storing multiple SRI questionnaires therein, and each of the at least one mobile electronic apparatus requests some of the multiple SRI questionnaires stored in the stress management server as the need arises, and outputs the some of the multiple SRI questionnaires received in response to the request.

In accordance with further aspect of the present invention, there is provided a system for managing stress by using a mobile electronic apparatus and a data management server, the system including: at least one mobile terminal; a stress management server; and a user terminal, wherein each of the at least one mobile terminal includes: a bio-signal measuring device for measuring a bio-signal of a user; a bio-signal pattern information generation unit for combining bio-signals, each of which is periodically received as an input from the bio-signal measuring device, and generating bio-signal pattern information; an individual reference information generation unit for outputting a Stress Response Inventory (SRI) questionnaire for checking a stress level of the user, receiving an answer to each question of the SRI questionnaire, driving the bio-signal measuring device and the bio-signal pattern information generation unit, and generating individual reference information obtained by connecting the result of answering the SRI questionnaire with the pattern information of the measured bio-signals; and a stress analysis request unit for transmitting the pattern information of the measured bio-signals to a stress management server, and requesting analysis of a stress level of the user, wherein the stress management server includes: a bio-signal pattern information management unit for receiving the bio-signal pattern information from the outside, and forming a bio-signal pattern information data base (DB) of the received bio-signal pattern information; a reference information management unit for receiving several pieces of the individual reference information from the outside, and forming an individual reference information data base (DB) of the several pieces of the individual reference information; a site operating unit for managing information including images, a hyperlink, and a web page used for site operation, and performing the site operation; a member information management unit for managing member information including identification information of each of the at least one mobile terminals, identification information of a user, a member IDentification (ID), and a pass word; and a stress information providing unit for providing stress information including a stress level corresponding to pattern information of bio-signals measured by the mobile terminal associated with the member ID.

In another aspect of the invention, the user terminal includes: an individual reference information management unit for transmitting the individual reference information received from each of the at least one mobile terminals to the stress management server; a reference information storage unit for receiving reference information from the stress management server, and storing the received reference information therein; and a stress level analysis unit for receiving a request for analysis of a stress level of the user from a specified mobile terminal, and analyzing the stress level based on bio-signal pattern information received from the specified mobile terminal.

BRIEF DESCRIPTION OF THE DRAWINGS

The above and other exemplary features, aspects, and advantages of the present invention will be more apparent from the following detailed description taken in conjunction with the accompanying drawings, in which:

FIG. 9 is an illustrative view of reference information stored in a DataBase (DB) to which the method for analyzing stress according to an embodiment of the present invention is applied.

DETAILED DESCRIPTION OF THE INVENTION

Exemplary embodiments of the present invention are described in detail with reference to the accompanying drawings. Particulars found in the following description of the present invention, such as specific configuration elements, etc., are provided to assist those skilled in the art with a comprehensive understanding of the present invention. Also, in the following description of the present invention, a detailed description of known functions and configurations incorporated, herein, will be omitted when it may make the subject matter of the present invention rather unclear.

Figure 1:
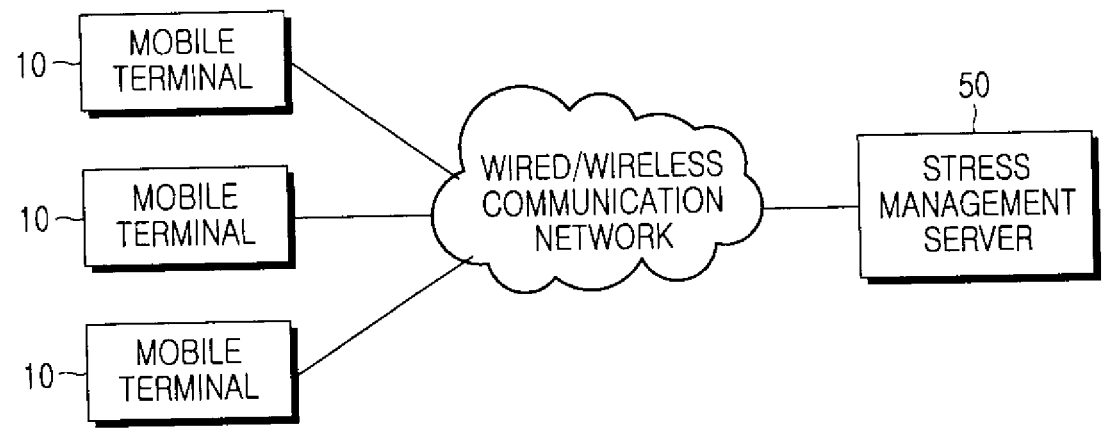
FIG. 1 is a block diagram illustrating a configuration of a stress management system according to an embodiment of the present invention.

FIG. 1 is a block diagram illustrating a configuration of a stress management system according to an embodiment of the present invention. Referring to FIG. 1, the stress management system according to an embodiment of the present invention includes multiple mobile terminals (all referred to with the same reference numeral "10") and a stress management server 50, which are connected to one another via wired/wireless communication networks.

In an embodiment of the present invention, the stress management system 50 performs a function of generating reference information forming the basis of stress analysis and a function of analyzing a stress level by using bio-signals of users of the multiple mobile terminals 10. Accordingly, each of the multiple mobile terminals 10 is implemented in order to operate in a mode for generating and providing individual reference information for generating the reference information and in a mode for requesting the analysis of a stress level of a user of a relevant mobile terminal 10. Also, the stress management server 50 is implemented in order to operate in a mode for combining several pieces of the individual reference information to form a DataBase (DB) of the reference information and in a mode for analyzing a stress level, as described above, to provide a result of analyzing a stress level.

A mobile terminal 10 provides a user with an interface through which the user of the mobile terminal 10 can select either of the two modes as described above (i.e. a mode for generating and providing individual reference information and a mode for requesting the analysis of a stress level of a user). For example, the mobile terminal 10 displays icons or characters respectively representing the two modes on an initial screen of a display(not shown) thereof, and receives user's input of each direction key (i.e. each arrow key) or each number key (not shown)., so that a mode of the mobile terminal 10 can be selected from the two modes by the user's input. When the mobile terminal 10 is set to the mode for generating and providing individual reference information by the user's selection, the mobile terminal 10 provides questions for checking a stress level of the user and multiple answer choices on each question through the display thereof, and receives as input the selection of at least one answer choice in response to each question. Also, the mobile terminal 10 receives as an input a bio-signal of the user as a user answering the questions, and analyzes a pattern of the received bio-signals to generate bio-signal pattern information. Further, the mobile terminal 10 combines the answers to the questions with the bio-signal pattern information to generate individual reference information, and transmits the generated individual reference information to the stress management server 50.

On the other hand, when the mobile terminal 10 is set to the mode for requesting the analysis of a stress level by the user's selection, the mobile terminal 10 receives as input a bio-signal of the user at predetermined intervals, and analyzes a pattern of the received bio-signals to generate bio-signal pattern information.

A function of the stress management server 50 is based on information transmitted by the mobile terminal 10. Namely, upon receiving an identifier for requesting the generation of reference information along with the individual reference information from the mobile terminal 10, the stress management server 50 stores the received individual reference information in a data base (DB) thereof in consideration of predetermined rules. Also, upon receiving an identifier for requesting the analysis of a stress level along with the bio-signal pattern information from the mobile terminal 10, the stress management server 50 checks the reference information stored in the data base (DB), searches for a stress level corresponding to the bio-signal pattern information, and transmits a result of the search back to the mobile terminal 10.

Figure 2:
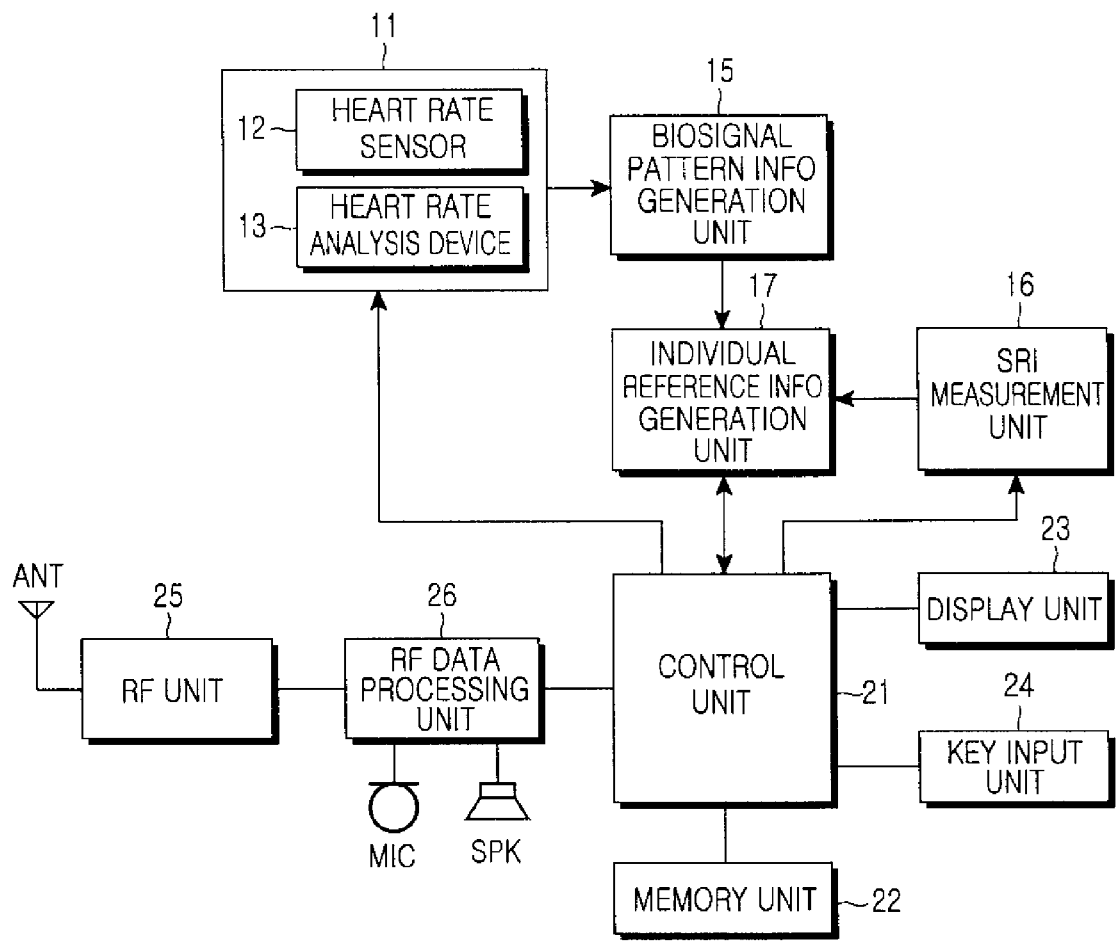
FIG. 2 is a block diagram illustrating a configuration of a mobile terminal included in the stress management system according to an embodiment of the present invention.

FIG. 2 is a block diagram illustrating a configuration of a mobile terminal 10 included in the stress management system according to an embodiment of the present invention. It can be noted from FIG. 2 that the mobile terminal 10, according to an embodiment of the present invention, can be applied to each of various apparatuses capable of having the functions as described above. Nevertheless, in an embodiment of the present invention, by citing a mobile communication terminal as an example of the mobile terminal 10, hardware apparatuses forming the basis, to which the present invention can be applied, will be described referring to the accompanying drawings.

Referring to FIG. 2, the mobile communication terminal included in the stress management system according to an embodiment of the present invention includes a bio-signal measurement module 11, a bio-signal pattern information generation unit 15, a Stress Response Inventory (SRI) measurement unit 16, an individual reference information generation unit 17, a control unit 21, a memory unit 22, a display unit 23, a key input unit 24, a Radio Frequency (RF) unit 25, and an RF data processing unit 26.

The bio-signal measurement module 11 is implemented so that a user can freely measure a bio-signal of the user by using a measuring device which can be carried by the user. For example, when a bio-signal intended to be measured is a heart rate of the user, the bio-signal measurement module 11 is attached to a part of the user's body to detect a heart rate of the user, and may include a mobile heart rate sensor 12 implemented in order to be able to carried by the user and a heart rate analysis device 13 for converting a signal provided by the mobile heart rate sensor 12 into standardized data.

The bio-signal pattern information generation unit 15 combines the bio-signals provided by the bio-signal measurement module 11, and generates bio-signal pattern information. The bio-signal pattern information is generated by using a bio-signal received as input at predetermined intervals. For example, bio-signal pattern information may correspond to information representing a pattern obtained by measuring a heart rate signal at least one time for each of five predetermined periods (i.e. from 9 to 12 o'clock, from 12 to 15 o'clock, from 15 to 18 o'clock, from 18 to 21 o'clock, and from 21 to 24 o'clock) and combining the measurement results, or the measurements may be made at a later of once per hour, for example, and the measurements combined every 4 hours, for example. In this illustrative case, the hourly measurements may be combined as groups with a combining time window (e.g., every 4 hours), or may be combined using a sliding window of a known time (e.g., every 4 hours). Although an example of the periods are described herein, it will understood by those skilled in the art that the period of measurement and the period of combining may be altered without undue experimentation.

The bio-signal pattern information generation unit 15 may include an alarm for informing the user that he/she can recognize the input of a bio-signal at every predetermined period. For example, when setting five predetermined periods (i.e. a first period from 9 to 12 o'clock (9 am-12 pm), a second period from 12 to 15 o'clock (12 pm-3 pm), a third period from 15 to 18 o'clock (3 pm-6 pm), a fourth period from 18 to 21 o'clock (6 pm-9 pm), and a fifth period from 21 to 24 o'clock (9 pm-midnight)), the alarm can be set so as to repeatedly give the user a warning as a bio-signal is measured at predetermined time intervals (e.g. at 10-minute intervals) is during any of the five predetermined periods. Even though the number of the predetermined periods is set to five in an embodiment of the present invention as described above, the present invention is not limited to this single configuration. The predetermined periods can be freely set by the user. To this end, the mobile communication terminal can be implemented so that the user can set predetermined periods by selecting a menu named "bio-signal pattern information setting" among menu items prepared for various function settings. Also, it goes without saying that predetermined periods may be fixed in order to have values properly set by a developer and the fixed predetermined periods can be provided to users.

The SRI measurement unit 16 displays, through the display unit 23, an SRI questionnaire selected from among multiple SRI questionnaires stored in the memory unit, and receives as input an answer or response to each question of the selected SRI questionnaire through the key input unit 24 and stores the responses to the selected SRI questionnaire in the memory unit 22.

The bio-signal pattern information generation unit 15 and the SRI measurement unit 16 are driven by a request of the individual reference information generation unit 17. The individual reference information generation unit 17 can be executed during the selection of a menu named "individual reference information generation" among a plurality of menu items included in the mobile communication terminal. At this time, the individual reference information generation unit 17 matches the bio-signal pattern information with the results from answering the SRI questionnaire, and generates individual reference information, where the bio-signal pattern information and the answer result are stored in the memory unit 22 during the operations of the bio-signal pattern information generation unit 15 and the SRI measurement unit 16.

The control unit 21 generally controls operations of the functional units by performing a function of controlling an overall operation of the mobile communication terminal. Namely, the control unit 21 controls the key input unit 24 so as to perform processing according to a detected input (e.g., a number) and a menu selection signal received as input through the key input unit 24, controls the bio-signal measurement module 11 so as to process a signal received as input through the bio-signal measurement module 11, controls the memory unit 22 so as to store the measured bio-signals and the obtained SRI information, and controls the bio-signal pattern information generation unit 15 and the individual reference information generation unit 17 so as to generate bio-signal pattern information and individual reference information by using the stored bio-signals and SRI information. Also, the control unit 21 controls the display unit 23 so as to display an SRI questionnaire for obtaining the SRI information, the generated bio-signal pattern information and individual reference information, etc. At this time, as the need arises, the control unit 21 controls the memory unit 22 so as to provide contents stored in the memory unit 22 which are to be output, or so as to store the contents. Also, the memory unit 22 stores therein multiple programs and multiple pieces of data related to the operation of the control unit 21.

In addition, upon receiving as input the selection of a menu named "stress level check" among the menu items included in the mobile communication terminal, the control unit 21 transmits the bio-signals and the bio-signal pattern information stored in the memory unit 22 to the stress management server 50, and requests stress analysis along with the transmission. When receiving a result of the stress analysis, the control unit 21 controls the memory unit 22 so as to store the result of the stress analysis, and controls the display unit 24 to display the result of the stress analysis so that the user can check the result of the stress analysis. Further, upon receiving a request for checking a stress level from the user, the control unit 21 controls the bio-signal pattern information generation unit 15 so as to operate in real time and generate bio-signal pattern information. When the bio-signal pattern information is generated, the control unit 21 transmits the bio-signal pattern information to a user terminal 30, and requests stress analysis along with the transmission. When receiving the result of the stress analysis, the control unit 21 controls the memory unit 22 so as to store the result of the stress analysis, and controls the display unit 24 so as to display and provide the result of the stress analysis.

The display unit 23 may be implemented by using a display device, such as a Liquid Crystal Display (LCD), etc., and displays not only messages indicating various operation states of the relevant terminal, but also photographed digital image data, under the control of the control unit 21. The key input unit 24 receives as input a telephone number or a character from the user, for example. To this end, the key input unit 24 includes keys for inputting numerals and characters and function keys for setting various functions, and outputs an input signal through each key to the control unit 21.

The RF unit 25 modulates voice data, character data, and control data of the user into an RF signal, and transmits the RF signal to a base station (not shown) of a mobile communication network. When receiving an RF signal from the base station, the RF unit 25 demodulates the received RF signal into voice data, character data, control data, etc., and outputs the data. Under the control of the control unit 21, the RF data processing unit 26 decodes voice data received by the RF unit 25, and outputs the decoded voice data as an audible sound through a speaker. Also, the RF data processing unit 26 converts a voice signal of the user received as input from a microphone into data and outputs the converted data to the RF unit 25, and provides character data and control data received as input through the RF unit 25 to the control unit 21.

The mobile terminal having the configuration as described above performs an operation related to a conventional mobile communication service. At this time, besides the functions as described above, the control unit 21 performs both a function of generating individual reference information and a function of checking a stress level based on bio-signals of the user, according to the features of the present invention.

Figure 3:
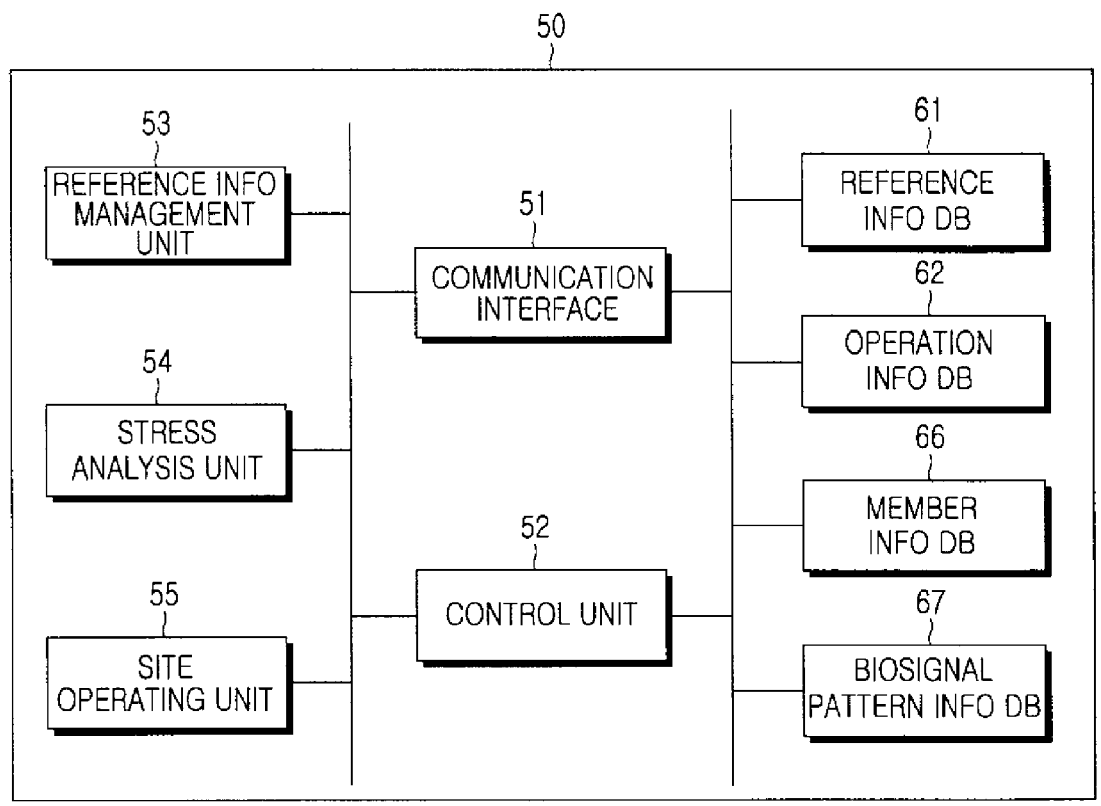
FIG. 3 is a block diagram illustrating a configuration of a stress management server included in the stress management system according to an embodiment of the present invention.

FIG. 3 is a block diagram illustrating a configuration of the stress management server 50 included in the stress management system according to an embodiment of the present invention. Referring to FIG. 3, the stress management server 50 according to an embodiment of the present invention includes a communication interface 51, a control unit 52, a reference information management unit 53, a stress analysis unit 54, and a reference information data base (DB) 61.

The communication interface 51 acts as an interface for transmitting data between the mobile terminal 10 and the stress management server 50, and can be implemented by using one of a plurality of known interfaces capable of transmitting data over wired/wireless communication networks.

The control unit 52 generally controls operations of the functional units by performing a function of controlling an overall operation of the stress management server 50. Namely, the control unit 52 checks data received via the communication interface 51, and directs operations of the reference information management unit 53 and the stress analysis unit 54, etc., according to commands included in the received data.

In consideration of a stress level and a result of answering an SRI questionnaire, the reference information management unit 53 stores individual reference information received from a mobile terminal 10 in the reference information DB 61, and manages the individual reference information.

Since various mental processes appear as dynamic changes of heartbeat intervals (i.e. RR intervals) through control of an autonomic nervous system, the analysis of a Heart Rate Variability (HRV) makes it possible to analyze a stress level. Particularly, a group suffering from chronic stress is hindered in a control action of the autonomic nervous system due to increased hormones, and therefore, has a slower HRV and undergoes a more frequently—occurring circadian rhythm of hormone production (i.e. a change of hormone production on a daily cycle) than normal people. Accordingly, with data on heartbeat intervals of normal people as reference, statistical analysis for each age group is performed on a ratio between low and high frequency components (an LF/HF ratio) from among parameters of an HRV and official values obtained from a height and a width of a histogram of the value of an HRV, so that it is possible to calculate a stress level.

Accordingly, in an embodiment of the present invention, a bio-signal may correspond to a signal obtained by measuring a heart rate, and bio-signal pattern information may include the value of measuring a heart rate for each period.

Figure 4:
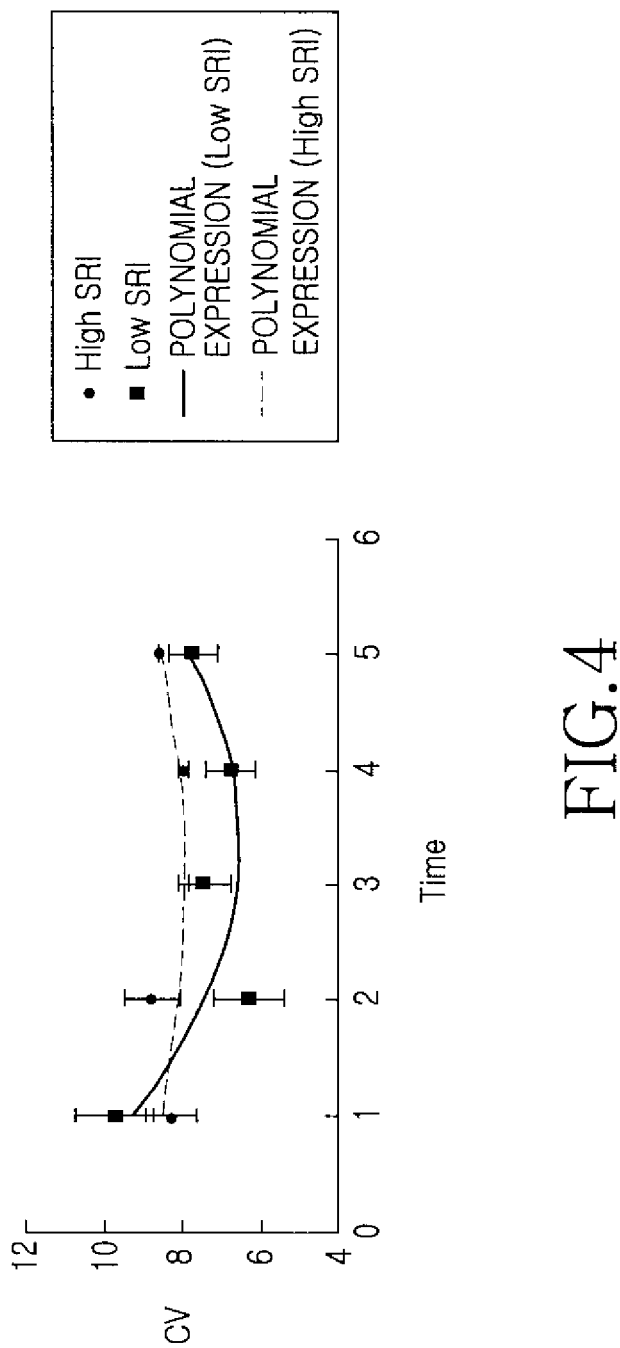
FIG. 4 is a graph showing a Circadian rhythm Variability (CV) with the lapse of time of bio-signal pattern information used as reference information by the stress management system according to an embodiment of the present invention.
Figure 5:
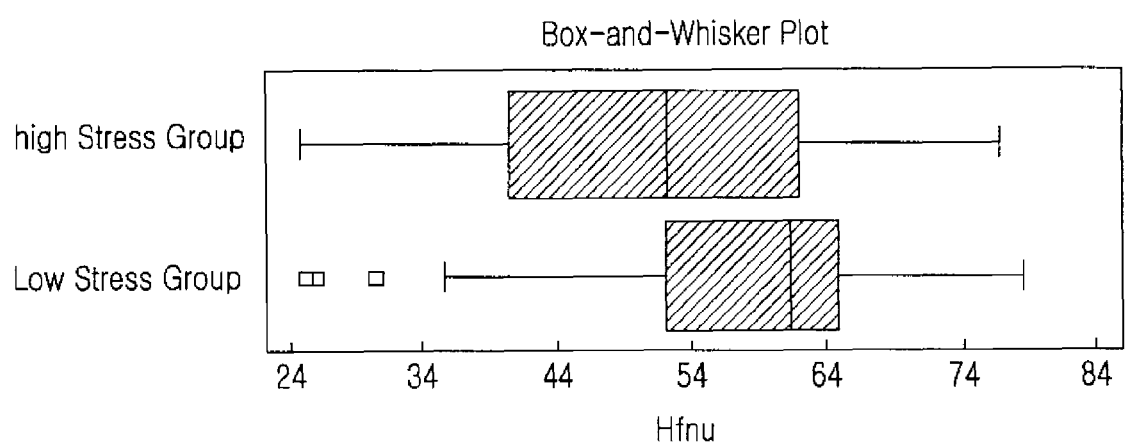
FIG. 5 is an illustrative view of a High-Frequency normalized unit (HFn.u.) used as reference information by the stress management system according to an embodiment of the present invention.

Also, the reference information management unit 53 classifies people answering their own SRI questionnaires into a high stress group and a low stress group based on the responses to each SRI questionnaire, and forms a reference of a stress level based on bio-signals received as input from subjects belonging to each group. For example, as in FIG. 4, the reference information management unit 53 performs curve fitting on a Circadian rhythm Variability (CV) of the bio-signal pattern information (i.e. a pattern of the bio-signal pattern information on a daily cycle) in order to find an equation (e.g., a quadratic or other higher order polynomial equation), thereby setting a reference of each group. Also, the reference information management unit 53 measures an HFn.u. as in FIG. 5, thereby setting a reference of each group.

Upon receiving a request for stress analysis from the mobile terminal 10, the stress analysis unit 54 analyzes stress based on the bio-signals and bio-signal pattern information. Specifically, the stress analysis unit 54 performs curve fitting on the bio-signal pattern information in order to find, for example, a quadratic equation, and defines a time point with an effective value (e.g. $p<0.05$) as a reference of the bio-signal pattern information. Also, the stress analysis unit 54 compares a variability of pattern information of input bio-signals with the reference of the bio-signal pattern information by using an F-test, and specify a change of the bio-signal pattern information for each date. Also, the stress analysis unit 54 compares an average of pattern information of bio-signals, which are measured and then received as input, with the reference of the bio-signal pattern information, and determines if a stress level is increased or decreased.

Meanwhile, the reference information data base DB 61 is used to classify and store information on a response to each SRI questionnaire, a stress level corresponding to response (s), the age and sex distinction of each user answering their own SRI questionnaire, etc., and individual reference information including bio-signal pattern information of each user, where several pieces of the information are managed in connection with one another. Accordingly, the stress analysis unit 54 can check a stress level corresponding to the bio-signal pattern information with reference to the reference information DB 61. Namely, when receiving a request for stress analysis along with the reception of the bio-signal pattern information from the mobile terminal 10, the stress analysis unit 54 checks the reference information DB 61, and extracts individual reference information corresponding to the bio-signal pattern information from the information stored in the reference information DB 61. Then, the stress analysis unit 54 checks a stress level included in the extracted individual reference information.

Also, the stress management server 50 can provide information related to stress through a web site. To this end, the stress management server 50 may further include a site operating unit 55, an operation information data base DB 62, a member information data base DB 66, and a bio-signal pattern information data base DB 67.

Herein, the site operating unit 55 operates a site according to an algorithm for driving a web site. The operation information data base DB 62 stores therein various data required for the site operation (e.g. operation information including a web page, images, a hyperlink, etc.). The member information data base DB 66 stores IDentification (ID) of a member subscribing to a site, an identification code of a user terminal of each member, etc. The bio-signal pattern information data base DB 67 stores bio-signal pattern information received from a mobile terminal 10 of each member.

Figure 6:
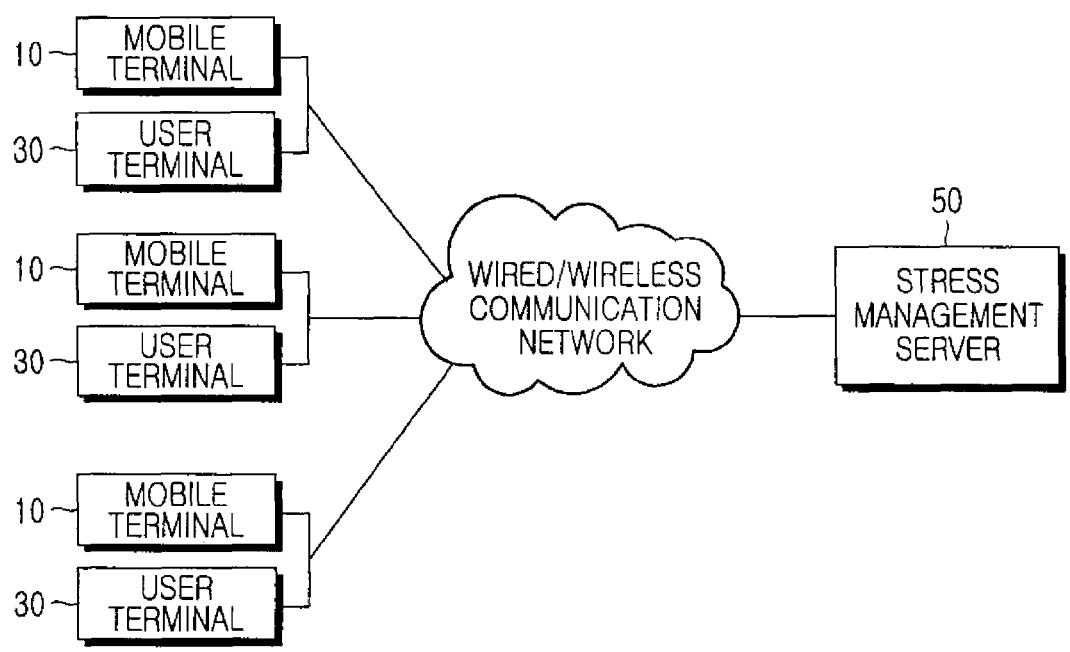
FIG. 6 a block diagram illustrating a configuration of a stress management system according to another embodiment of the present invention.

FIG. 6 a block diagram illustrating a configuration of a stress management system according to another embodiment of the present invention. Referring to FIG. 6, the stress management system according to another embodiment of the present invention may further include a user terminal 30 as a configuration apparatus for mediating between a mobile terminal 10 and the stress management server 50 according to an embodiment of the present invention.

The user terminal 30 may be implemented by using a conventional Personal Computer (PC) loaded with a stress management program. The user terminal 30 can be implemented in order to perform the function of the stress analysis unit 54 of the stress management server 50 according to an embodiment of the present invention. Also, upon receiving, as the need arises, information stored in the reference information data base DB 61 from the stress management server 50, the user terminal 30 can store and manage the received information. Since the user terminal 30 performs the stress analysis function, the stress management server 50 does not need to include the stress analysis unit 54.

In another aspect, the stress management server 50 can provide not only a stress level corresponding to a measured bio-signal, but also various methods for relieving stress in response to the stress level. For example, the stress management server 50 can receive a treatment corresponding to a stress level, etc., from a user with expertise on stress (e.g. a psychiatrist), and provide the received treatment.

A detailed description of a method for analyzing stress according to the present invention with reference to the accompanying drawings.

Figure 7:
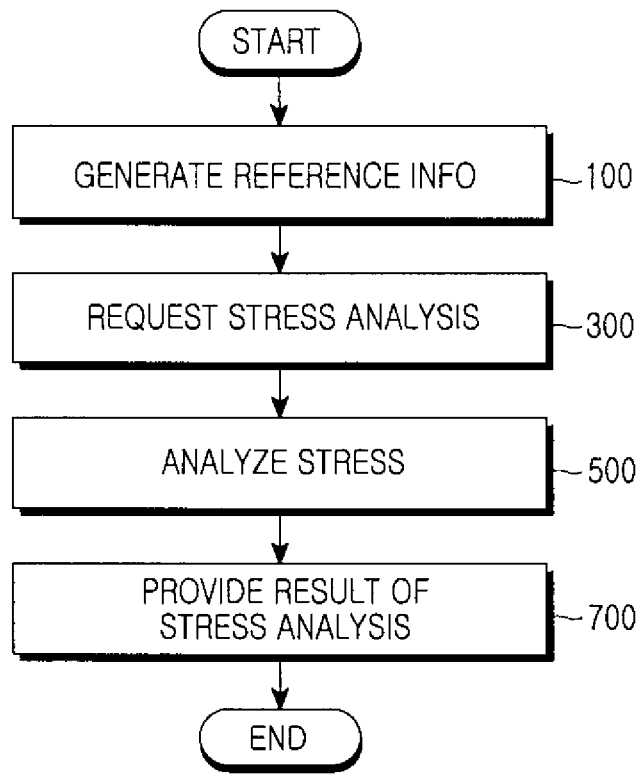
FIG. 7 is a flowchart showing a method for analyzing stress according to an embodiment of the present invention.
Figure 8:
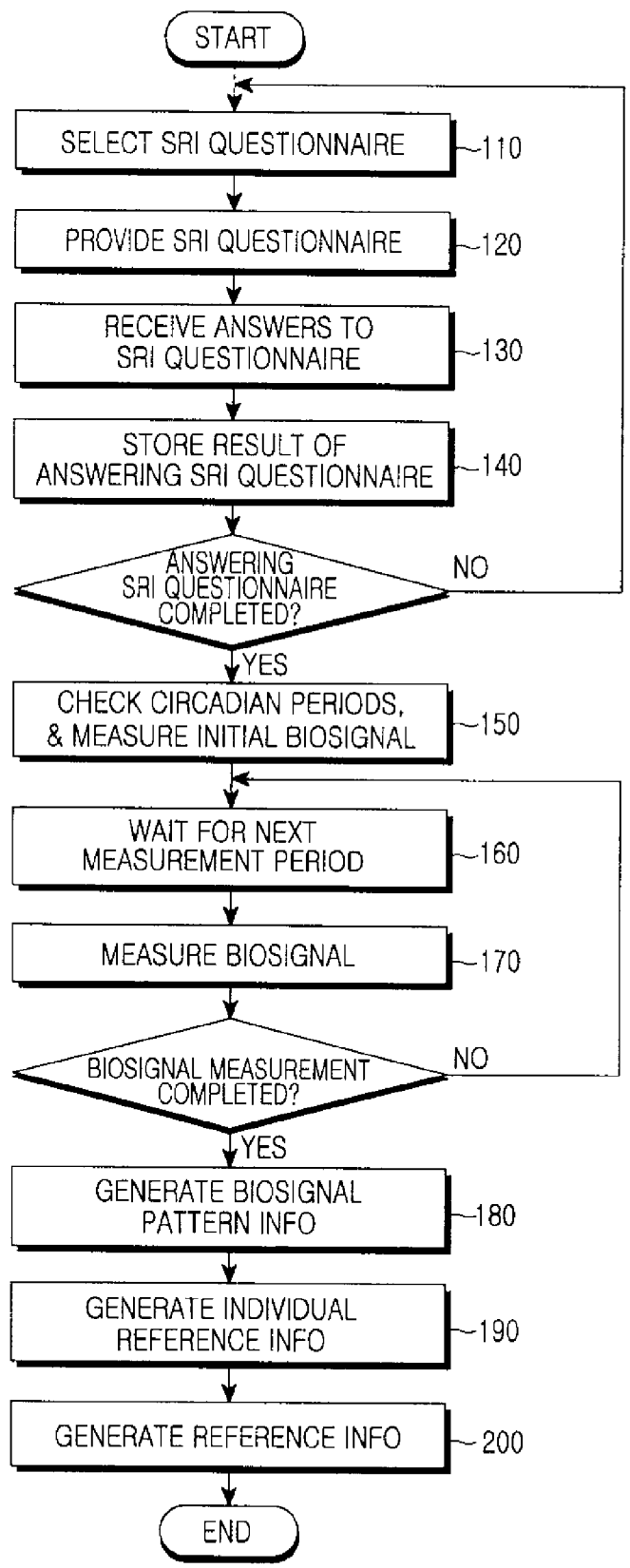
FIG. 8 is a flowchart showing in detail a process in step 100 of FIG. 7.

FIG. 7 is a flowchart showing a method for analyzing stress according to an embodiment of the present invention, and FIG. 8 is a flowchart showing in detail a process shown in step 100 of FIG. 7. Referring to FIGS. 7 and 8, in the method for analyzing stress according to an embodiment of the present invention, before performing stress analysis, reference information is generated in order to discriminate between a normal group and a stress group during the stress analysis (step 100).

Preferably, step 100 is performed by learning both a result of answering questions included in an SRI questionnaire and a bio-signal which are received as input from each of unspecified individuals, and may include steps 110 to 200 (refer to FIG. 8). First, step 110 is performed by selecting a menu for generating reference information among menu items included in a mobile phone by a user. For example, when the menu for generating reference information is a menu named "generation of individual reference information," step 110 is performed by selecting the menu named "generation of individual reference information" by the user. When the menu named "generation of individual reference information" is selected, the mobile terminal first receives as input user characteristics, such as age, sex, etc., of the user, and selects an SRI questionnaire corresponding to the input characteristic, (e.g., age, sex, etc.), among all SRI questionnaires stored in the memory unit. Then, the mobile terminal displays the selected SRI questionnaire, including multiple SRI questions and multiple answer choices on each of the multiple SRI questions, on a screen (step 120), receives as an input responses to the displayed SRI questionnaire (step 130), and stores the input responses (step 140). Steps 120, 130, and 140 are repeatedly performed until an answer to each of the selected SRI questions is received (or until the user indicates that enough responses have been provided). When an answer to each of the selected SRI questions is completed, the mobile terminal measures a bio-signal of the user answering the selected SRI questionnaire. A bio-signal is measured in consideration of a CV in order to check a change of a bio-signal on a 24-hour cycle. For example, a daily cycle can be divided into a first period from 9 to 12 o'clock, a second period from 12 to 15 o'clock, a third period from 15 to 18 o'clock, a fourth period from 18 to 21 o'clock, and a fifth period from 21 to 24 o'clock. Then, a bio-signal of the user answering the SRI questionnaire is measured at least one time during each period. Namely, if the performance of step 140 is completed, by performing step 150, a period corresponding to a completed time point is checked, and at least one bio-signal is measured at least one time during the period. Then, until reaching the next period, the measurement of a bio-signal is in a waiting state (step 160). When reaching the next period, a bio-signal is again measured (step 170). Steps 160 and 170 are repeatedly performed until a bio-signal is measured at least one time for each of the first through fifth periods. Herein, through the mobile terminal, the user can set either of two parameters: the number of times of measuring a bio-signal in each period (e.g. a bio-signal is measured three times in each period for 24 hours from a time point of completing the performance of step 140), and the number of times of measuring a bio-signal at every daily cycle (e.g. a bio-signal is measured for three days in such a condition that the bio-signal is measured once during each period).

Further, the present invention does not limit the number of times of measuring a bio-signal, and the number of times of measuring a bio-signal may be determined according to an algorithm for generating reference information forming the basis of stress analysis. Next, if the measurement of a bio-signal during a daily cycle is completed, step 180 is performed. In step 180, bio-signal pattern information is generated, which includes a pattern of bio-signals measured during a daily cycle. For example, curve fitting is performed on bio-signals measured during a daily period in order to find a quadratic equation, for example, effective points are determined among points on which the curve fitting is performed, and a pattern formed by the effective points is generated as the bio-signal pattern information. Then, individual reference information is generated which is obtained by connecting the bio-signal pattern information with the result of answering the SRI questionnaire (step 190). The generated individual reference information can be provided to the stress management server, and several pieces of individual reference information as provided above are stored in the stress management server. Finally, the stress management server combines several pieces of individual reference information respectively provided by multiple users, and generates several pieces of reference information classified according to predetermined criteria (e.g. a stress level according to sex and/or each age) (step 200). Step 100 can be continuously and repeatedly performed by a request of a user of a mobile terminal, and the reference information can be continuously updated through learning. Further, as individual reference information from each of many and unspecified users is continuously updated, more pieces of bio-signal pattern information of users belonging to each of various groups and more various samples can be secured. Accordingly, stress can be more accurately analyzed.

Step 200 is performed by selecting a menu for requesting stress analysis (e.g. a menu named "stress analysis") among menu items included in the mobile terminal by the user.

Specifically, upon receiving as input the selection of the menu for stress analysis from the user, the mobile terminal measures a bio-signal of the user, and generates bio-signal pattern information. A process for measuring a bio-signal and a process for generating bio-signal pattern information are achieved through the same process as a process for performing steps 150, 160, 170, and 180 as described above. When the bio-signal pattern information is generated as described above, the bio-signal pattern information is transmitted to an apparatus (e.g. the stress management server) for analyzing a stress level by using the reference information, and requests the apparatus to analyze stress.

Even though the mobile terminal receives as input the selection of a menu for stress analysis from the user and generates bio-signal pattern information in an embodiment of the present invention, the present invention is not limited to this. For example, a user may previously measure his/her own bio-signals, generate pattern information of the measured bio-signals, and then store the generated bio-signal pattern information in a mobile terminal of the user. Then, as the need arises, the user may select the stored bio-signal pattern information, and request stress analysis.

Next, the apparatus (e.g. the stress management server or user terminal 30, FIG. 6) for analyzing a stress level receives the bio-signal pattern information, and checks a stress level corresponding to the received bio-signal pattern information (step 500). Specifically, the apparatus checks a polynomial equation of known order (e.g., quadratic is of order 2) of bio-signal pattern information of a group corresponding to the sex or age of the user whose bio-signal has been measured within the reference information, and extracts individual reference information having bio-signal pattern information similar in form to, for example, a quadratic equation of the pattern information of the measured bio-signals. Then, the apparatus checks a result of answering an SRI questionnaire included in the extracted individual reference information, checks a stress level based on the answer result, and then determines the checked stress level as a stress level of the user.

FIG. 9 is an illustrative view of reference information stored in a data base DB to which the method for analyzing stress according to an embodiment of the present invention is applied. Referring to FIG. 9, as an example, it is assumed that sex and age received as input from a user requesting stress measurement are respectively the male sex and "31," and a quadratic equation of pattern information of measured bio-signals is "$X^2+X+3$." Since the quadratic equation of the pattern information of the measured bio-signals is similar to a quadratic equation of bio-signal pattern information of an identification number "130002" within the reference information, the identification number "130002" is extracted as individual reference information. Then, a stress level of the extracted individual reference information is checked.

The checked stress level is transmitted back to the mobile terminal, and the mobile terminal displays the result (e.g. the checked stress level) transmitted back thereto on a screen thereof (step 700).

In the method for analyzing stress according to the present invention, the stress management server receives individual reference information provided by each of the multiple mobile terminals, generates and updates reference information by using the several pieces of individual reference information, analyzes stress by using the updated reference information, and then provides a result of analyzing stress. Nevertheless, the present invention is not limited to this, and it goes without saying that various methods for analyzing stress can be performed by a system including the multiple mobile terminals and the stress management server, etc. For example, the stress management server may perform only the function of receiving individual reference information provided by each of the multiple mobile terminals, generating reference information, and providing the generated reference information to a user terminal (e.g. a conventional personal computer). On the other hand, the user terminal may store, in a separate memory, reference information stored in the stress management server, continue to update the reference information, and analyze stress by using the reference information and a stress analysis tool stored in the user terminal.

The above-described methods according to the present invention can be realized in hardware or as software or computer code that can be stored in a recording medium such as a CD ROM, an RAM, a floppy disk, a hard disk, or a magneto-optical disk or downloaded over a network, so that the methods described herein can be executed by such software using a general purpose computer, or a special processor or in programmable or dedicated hardware, such as an ASIC or FPGA. As would be understood in the art, the computer, the processor or the programmable hardware include memory components, e.g., RAM, ROM, Flash, etc. that may store or receive software or computer code that when accessed and executed by the computer, processor or hardware implement the processing methods described herein.

While the invention has been shown and described with reference to certain exemplary embodiments thereof, it will be understood by those skilled in the art that various changes in form and details may be made therein without departing from the spirit and scope of the invention. Therefore, the spirit and scope of the present invention must be defined not by described embodiments thereof but by the appended claims and equivalents of the appended claims.

What is claimed is:

1. A method for analyzing stress, the method comprising the steps of:
   generating bio-signal pattern information upon periodically receiving a bio-signal from a plurality of bio-signal measuring devices each connected to one of a plurality of unspecified individuals;
   receiving an answer to each of a plurality of questions for checking a stress level, said questions being provided to each of the unspecified individuals in accordance with at least one physical characteristic of the unspecified individuals;
   forming a reference information collection for stress analysis based on the bio-signal pattern information corresponding to the unspecified individuals and the answers received, wherein the reference information is classified according to criteria associated with characteristics of the unspecified individuals;
   receiving bio-signal pattern information from one of the plurality of bio-signal measuring devices connected to a specified user, wherein the bio-signal pattern information of the specified user is determined from a plurality of bio-signals obtained from the one of the plurality of bio-signal measuring devices over a predetermine period;
   determining, by a processor, a reference information from said reference information collection, said determined reference information substantially matching the bio-signal pattern information from the one of the plurality of bio-signal measuring devices connected to the specified user, said determined reference information being associated with at least one characteristic associated with the specified user; and
   determining, by the processor, a stress level corresponding to the bio-signal pattern information of the specified user based on the determined reference information, for display.

2. The method as claimed in claim 1, further comprising a step of:
   displaying additionally included information enabling reduction of a stress level in response to the determined stress level.

3. The method as claimed in claim 1, wherein the step of generating bio-signal pattern information comprises the sub-steps of:
   providing the plurality of questions to each of the unspecified individuals,
   determining a stress level of each of the unspecified individuals upon receiving an answer to each of the plurality of questions;
   generating bio-signal pattern information upon periodically receiving a bio-signal from each of the bio-signal measuring devices;
   storing the bio-signal pattern information in association with the determined stress level; and
   forming the reference information collection for stress analysis in consideration of the bio-signal pattern information and the determined stress level of the unspecified individuals.

4. The method as claimed in claim 1, wherein the bio-signal corresponds to a Heart Rate Variability (HRV), and is measured by a mobile sensor for sensing a heart rate and a heart rate measurement module for converting a signal received as an input from the mobile sensor into data representing an HRV.

5. The method as claimed in claim 4, wherein the heart rate measurement module requests measurement of a bio-signal at a predetermined cycle.

6. The method as claimed in claim 4, wherein the heart rate measurement module is mounted in a mobile terminal.

7. The method as claimed in claim 4, wherein the bio-signal pattern information includes one of: a maximum value and a minimum value of a periodically-measured HRV.

8. A system for managing stress by using a mobile electronic apparatus and a data management server, the system comprising:
   a plurality of mobile electronic apparatuses; and
   a stress management server,
   wherein each of the plurality of mobile electronic apparatuses comprises:
   a bio-signal measuring device configured for measuring a bio-signal of a user;
   a bio-signal pattern information generation unit configured for generating bio-signal pattern information by combining the bio-signals, each of which is periodically received as an input from the bio-signal measuring device;
an individual reference information generation unit configured for:
outputting a Stress Response Inventory (SRI) questionnaire for checking a stress level of the user, said questionnaire including a plurality of questions,
wherein said questions are provided to the user in accordance with at least one characteristic of the user,
receiving an answer to each of said plurality of questions of the SRI questionnaire,
driving the bio-signal measuring device and the bio-signal pattern information generation unit, and
generating individual reference information obtained by associating the received answers of the SRI questionnaire with the bio-signal pattern information of the corresponding measured bio-signals; and
a stress analysis request unit configured for:
transmitting the bio-signal pattern information of the measured bio-signals to the stress management server, and
requesting analysis of a stress level,
wherein the stress management server comprises:
a reference information management unit configured for receiving the individual reference information from each of the plurality of mobile electronic apparatuses, and
forming a DataBase (DB) of several pieces of the individual reference information, wherein the reference information is classified according to criteria associated with the characteristics of users associated with each of the plurality of mobile electronic apparatuses;
a bio-signal pattern information management unit configured for forming a DB of the bio-signal pattern information received from each of the plurality of mobile electronic apparatus; and
a stress level analysis unit configured for:
receiving the request for analysis of the stress level of a user associated with a specified one of the plurality of mobile electronic apparatuses;
determining a reference information from said database of reference information, said determined reference information substantially matching the bio-signal pattern information from the bio-signal measuring device connected to the user associated with a specific one of the plurality of mobile electronic apparatuses, said determined reference information being associated with at least one characteristic associated with the user associated with a specific one of the plurality of mobile electronic apparatuses; and
determining the stress level of the user from the determined reference information.

9. The system as claimed in claim 8, wherein the stress management server further comprises:
a site operating unit configured for managing data required for site operation; and
a member information management unit configured for:
managing member information including identification information of each of the plurality of mobile electronic apparatuses, identification information of a corresponding user, a site IDentification (ID), and a pass word.

10. The system as claimed in claim 8, wherein the bio-signal corresponds to a Heart Rate Variability (HRV), and wherein the bio-signal measuring device comprises:
a mobile sensor configured for sensing a heart rate; and
a heart rate measurement module configured for converting a signal received as an input from the mobile sensor into data representing an HRV.

11. The system as claimed in claim 10, wherein the heart rate measurement module comprises an alarm for requesting measurement of a bio-signal at a predetermined cycle.

12. The system as claimed in claim 10, wherein the bio-signal pattern information includes one of: a maximum value and a minimum value of a periodically-measured HRV.

13. The system as claimed in claim 10, wherein each of the plurality of mobile electronic apparatuses is mounted in a mobile communication terminal.

14. The system as claimed in claim 8, wherein each of the plurality of mobile electronic apparatuses comprises a storage medium configured for storing multiple SRI questionnaires therein, and selectively outputs at least one of the multiple SRI questionnaires.

15. The system as claimed in claim 8, wherein the stress management server comprises a storage medium configured for storing multiple SRI questionnaires therein; and wherein each of the plurality of mobile electronic apparatuses requests at least one of the multiple SRI questionnaires stored in the stress management server, and the stress management server outputs at least one of the multiple SRI questionnaires in response to the corresponding request from each of the plurality of mobile electronic apparatuses.

16. A system for managing stress by using a mobile electronic apparatus and a data management server, the system comprising:
a plurality of mobile terminals;
a stress management server; and
a user terminal,
wherein each of the plurality of mobile terminals comprises:
a bio-signal measuring device configured for measuring a bio-signal of an associated user;
a bio-signal pattern information generation unit configured for generating bio-signal pattern information by combining the bio-signals, each of which is periodically received as an input from the bio-signal measuring device;
an individual reference information generation unit configured for:
outputting a Stress Response Inventory (SRI) questionnaire to one of the plurality of mobile terminals for checking a stress level of the user associated with the one of the plurality of mobile terminals, wherein questions in the questionnaire are based on at least one characteristic of the user associated with the one of the plurality of mobile terminals,
receiving an answer to each question of the SRI questionnaire,
driving the bio-signal measuring device and the bio-signal pattern information generation unit, and
generating individual reference information obtained by associating the answers to the questions of the SRI questionnaire with the bio-signal pattern information of the measured corresponding bio-signals; and a stress analysis request unit configured for:
transmitting the bio-signal pattern information of the measured bio-signals to the stress management server, and
receiving a request for an analysis of a stress level of a user associated with one of the plurality of mobile terminals,
wherein the stress management server comprises:
a bio-signal pattern information management unit configured for:

receiving the bio-signal pattern information, and
forming a database (DB) of the received bio-signal pattern information;
a reference information management unit configured for:
receiving several pieces of the individual reference information, and
forming a DB of the several pieces of the individual reference information,
wherein the reference information is classified according to criteria associated with the characteristics of the user associated with the one of the plurality of mobile terminals;
a site operating unit configured for:
managing information including images, a hyperlink, and a web page used for site operation, and
performing the site operation;
a member information management unit configured for managing member information including identification information of each of the plurality of mobile terminals, identification information of a user associated with each of the plurality of mobile terminals, a member IDentification (ID), and a pass word; and
a stress information providing unit configured for:
providing, on a web page, stress information including a stress level corresponding to bio-signal pattern information of bio-signals measured by the one of the plurality of mobile terminals associated with a select one of the member ID, and
wherein the user terminal comprises:
an individual reference information management unit configured for:
transmitting the individual reference information received from each of the plurality of mobile terminals to the stress management server;
a reference information storage unit configured for:
receiving reference information from the stress management server, and
storing the received reference information therein; and
a stress level analysis unit configured for:
receiving a request for analysis of a stress level of a user associated with a specified one of the plurality of mobile terminals;
determining a reference information from said database of reference information, said determined reference information substantially matching the bio-signal pattern associated with the user associated with a specific one of the plurality of mobile terminals, said determined reference information being associated with at least one characteristic associated with the user associated with a specific one of the plurality of mobile terminals; and
determining the stress level based on bio-signal pattern information received from the specified one of the plurality of mobile terminals with respect to the determined reference information.

17. A device for analyzing stress, comprising:
a processor in communication with a memory, the memory containing code which when accessed by the processor causes the processor to execute the steps of:
generating bio-signal pattern information upon periodically receiving a bio-signal from a plurality of bio-signal measuring devices each connected to one of a plurality of unspecified individuals; and
receiving an answer to each of a plurality of questions for checking a stress level, said questions being provided to each of the unspecified individuals in accordance with at least one characteristic of the unspecified individuals;
forming a reference information collection for stress analysis based on the bio-signal pattern information corresponding to the unspecified individuals and the answers received, wherein the reference information is classified according to criteria associated with selected ones of characteristics of the unspecified individuals;
receiving bio-signal pattern information from one of the plurality of bio-signal measuring devices connected to a specified user, wherein the bio-signal pattern information of the specified user is determined from a plurality of bio-signals obtained from the one of the plurality of bio-signal measuring devices over a predetermined period;
determining a reference information from said reference information collection, said determined reference information substantially matching the bio-signal pattern associated with the specified user, said determined reference information being associated with at least one characteristic associated with the specified user; and
determining a stress level corresponding to the bio-signal pattern information of the specified user based on the determined reference information, for display.

* * * * *